US012651647B2

(12) United States Patent
Min et al.

(10) Patent No.: US 12,651,647 B2
(45) Date of Patent: Jun. 9, 2026

(54) PEPTIDE SEARCH SYSTEM FOR IMMUNOTHERAPY

(71) Applicant: NEC Laboratories America, Inc., Princeton, NJ (US)

(72) Inventors: Renqiang Min, Princeton, NJ (US); Hans Peter Graf, South Amboy, NJ (US); Ziqi Chen, Columbus, OH (US)

(73) Assignee: NEC Corporation, Tokyo (JP)

( * ) Notice: Subject to any disclaimer, the term of this patent is extended or adjusted under 35 U.S.C. 154(b) by 906 days.

(21) Appl. No.: 17/898,662

(22) Filed: Aug. 30, 2022

(65) Prior Publication Data

US 2023/0083313 A1    Mar. 16, 2023

Related U.S. Application Data

(60) Provisional application No. 63/243,404, filed on Sep. 13, 2021.

(51) Int. Cl.
G16B 40/00    (2019.01)
G06N 3/08    (2023.01)
G16B 15/30    (2019.01)

(52) U.S. Cl.
CPC ............... G16B 40/00 (2019.02); G06N 3/08 (2013.01); G16B 15/30 (2019.02)

(58) Field of Classification Search
CPC .......... G16B 40/00; G16B 15/30; G06N 3/08
See application file for complete search history.

(56) References Cited

U.S. PATENT DOCUMENTS

2015/0278441 A1* 10/2015 Min ....................... G16B 40/20
                                                    706/12
2019/0259474 A1*  8/2019 Wang .................... G16B 40/20

OTHER PUBLICATIONS

O'Donnell, T. J., Rubinsteyn, A., & Laserson, U. (Jul. 22, 2020). MHCflurry 2.0: improved pan-allele prediction of MHC class I-presented peptides by incorporating antigen processing. Cell systems, 11(1), 42-48.

* cited by examiner

*Primary Examiner* — Haimei Jiang
*Assistant Examiner* — Thomas Bernard Lane
(74) *Attorney, Agent, or Firm* — Vincent Duffy

(57)    ABSTRACT
A system for binding peptide search for immunotherapy is presented. The system includes employing a deep neural network to predict a peptide presentation given Major Histocompatibility Complex allele sequences and peptide sequences, training a Variational Autoencoder (VAE) to reconstruct peptides by converting the peptide sequences into continuous embedding vectors, running a Monte Carlo Tree Search to generate a first set of positive peptide vaccine candidates, running a Bayesian Optimization search with the trained VAE and a Backpropagation search with the trained VAE to generate a second set of positive peptide vaccine candidates, using a sampling from a Position Weight Matrix (sPWM) to generate a third set of positive peptide vaccine candidates, screening and merging the first, second, and third sets of positive peptide vaccine candidates, and outputting qualified peptides for immunotherapy from the screened and merged sets of positive peptide vaccine candidates to support downstream clinical decision making.

20 Claims, 4 Drawing Sheets

START

Train a deep neural network or employ a pre-trained model to predict a peptide presentation given an MHC allele sequence and a peptide sequence — 101

Train a VAE to reconstruct peptides and generate new peptides, converting peptide sequences into continuous embedding vectors — 103

Given a target MHC, run a Monte Carlo Tree Search to generate some peptide vaccine candidates and run a Bayesian Optimization and Backpropagation, and use the trained VAE decoder to generate some positive peptide vaccine candidates — 105

Given a target MHC, use sPWM to generate some positive peptide candidates — 107

Use MHCFlurry 2.0 to screen these merged positive peptide candidates to output a final set of positive peptides — 109

Output qualified peptides for immunotherapy from the screened and merged sets of positive peptide candidates and calculate the binding motif based on the qualified peptides for the target MHC — 111

END

300

Peptide

Monte Carlo Tree Search (MCTS) 560

Bayesian Optimization with VAE (BO-VAE) 562

Backpropagation with VAE (BP-VAE) 564 sampling with Positive Weight Matrix (sPWM) 566

310

Qualified Peptide 1

Qualified Peptide 2

Qualified Peptide 3

312

314

PEPTIDE SEARCH SYSTEM FOR IMMUNOTHERAPY

RELATED APPLICATION INFORMATION

This application claims priority to Provisional Application No. 63/243,404 filed on Sep. 13, 2021, the contents of which are incorporated herein by reference in their entirety.

BACKGROUND

Technical Field

The present invention relates to peptide generation and, more particularly, to a peptide search system with several search methods for immunotherapy.

Description of the Related Art

Foreign peptides bound to Major Histocompatibility Complex (MHC) class I proteins and presented on cell surfaces play a vital role in immunotherapy. These peptides can be recognized by T cell receptors to trigger an adaptive immune response.

SUMMARY

A system composed of several methods for searching for binding peptides is presented. The system includes employing a deep neural network to predict a peptide presentation given Major Histocompatibility Complex (MHC) allele sequences and peptide sequences, training a Variational Autoencoder (VAE) to reconstruct peptides by converting the peptide sequences of variable lengths into continuous embedding vectors of a fixed size, running a Monte Carlo Tree Search (MCTS) to generate a first set of positive peptide vaccine candidates. running a Bayesian Optimization search with the trained VAE (BO-VAE) and a Backpropagation search with the trained VAE (BP-VAE) to generate a second set of positive peptide vaccine candidates, using a sampling from a Position Weight Matrix (sPWM) to generate a third set of positive peptide vaccine candidates, screening and merging the first, second, and third sets of positive peptide vaccine candidates, and outputting qualified peptides for immunotherapy from the screened and merged first, second, and third sets of positive peptide vaccine candidates.

A non-transitory computer-readable storage medium comprising a computer-readable program for searching for binding peptides for immunotherapy is presented. The computer-readable program when executed on a computer causes the computer to perform the steps of employing a deep neural network to predict a peptide presentation given Major Histocompatibility Complex (MHC) allele sequences and peptide sequences, training a Variational Autoencoder (VAE) to reconstruct peptides by converting the peptide sequences of variable lengths into continuous embedding vectors of a fixed size, running a Monte Carlo Tree Search (MCTS) to generate a first set of positive peptide vaccine candidates, running a Bayesian Optimization search with the trained VAE (BO-VAE) and a Backpropagation search with the trained VAE (BP-VAE) to generate a second set of positive peptide vaccine candidates, using a sampling from a Position Weight Matrix (sPWM) to generate a third set of positive peptide vaccine candidates, screening and merging the first, second, and third sets of positive peptide vaccine candidates, and outputting qualified peptides for immunotherapy from the screened and merged first, second, and third sets of positive peptide vaccine candidates.

A system for searching for binding peptides is presented. The system includes a memory and one or more processors in communication with the memory configured to employ a deep neural network to predict a peptide presentation given Major Histocompatibility Complex (MHC) allele sequences and peptide sequences, train a Variational Autoencoder (VAE) to reconstruct peptides by converting the peptide sequences of variable lengths into continuous embedding vectors of a fixed size, run a Monte Carlo Tree Search (MCTS) to generate a first set of positive peptide vaccine candidates, run a Bayesian Optimization search with the trained VAE (BO-VAE) and a Backpropagation search with the trained VAE (BP-VAE) to generate a second set of positive peptide vaccine candidates, using a sampling from a Position Weight Matrix (sPWM) to generate a third set of positive peptide vaccine candidates, screen and merge the first, second, and third sets of positive peptide vaccine candidates, and output qualified peptides for immunotherapy from the screened and merged first, second, and third sets of positive peptide vaccine candidates.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
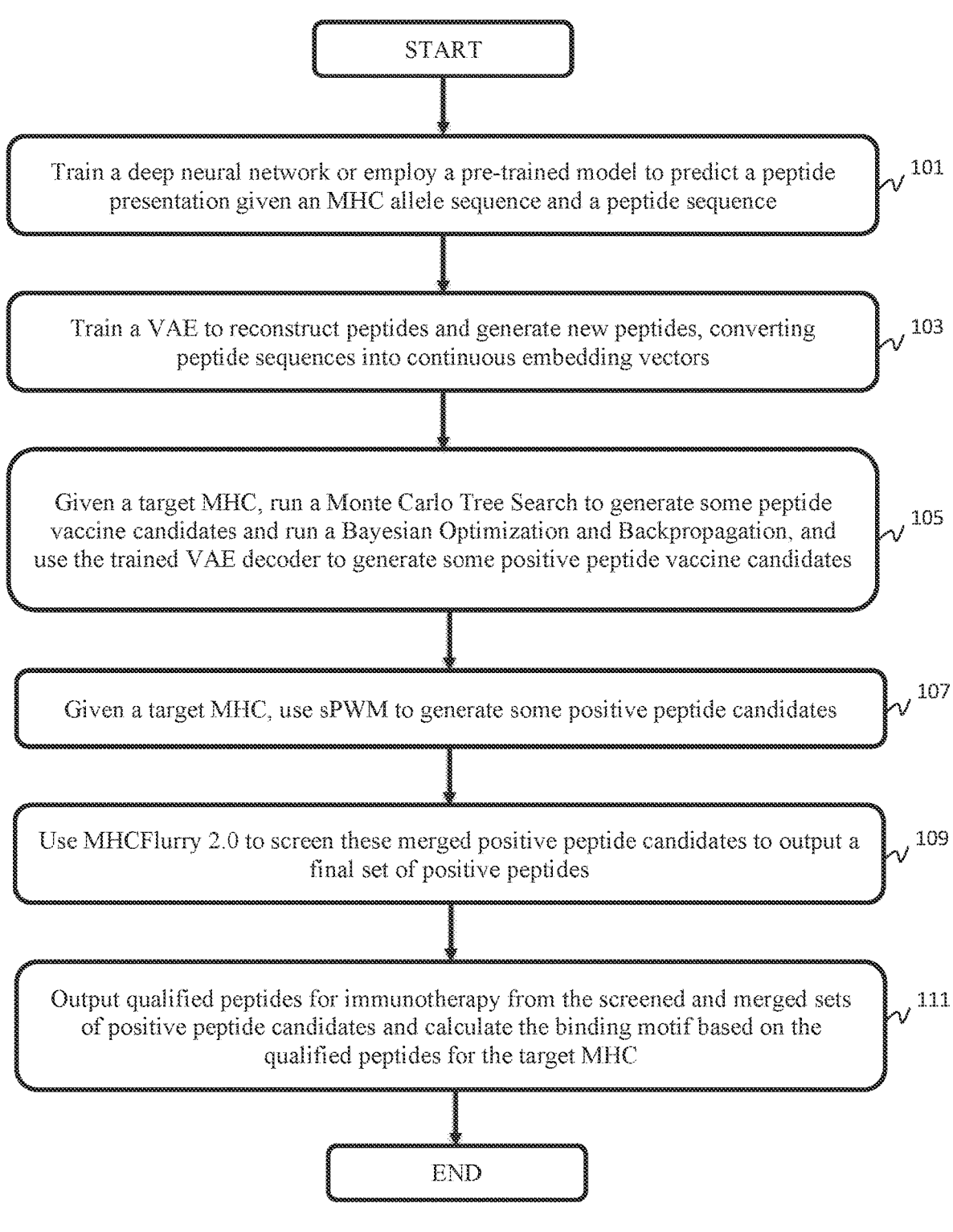
FIG. 1 is a block/flow diagram of an exemplary method for searching for peptide vaccine design for immunotherapy and peptide binding motif calculation based on identified qualified peptides, in accordance with embodiments of the present invention.

Immunotherapy, which aims at boosting a patient's immune system against intracellular pathogens (e.g., viruses or bacteria) and tumor cells, is a fundamental treatment for human diseases. A major branch of such immune responses are triggered by the Cytotoxic T cells (also known as CD8+ T cells) when they recognize foreign peptides presented by Major Histocompatibility Complex (MHC) Class I proteins on the cell surface. To attain recognition, these foreign peptides are first degraded from intracellular antigens by proteolytic enzymes within the proteasome, and then transported to the endoplasmic reticulum to bind to MHC Class I proteins. The resulting peptide-MHC complexes are then moved to the cell surface to interact with the CD8+ T cell receptors.

Leveraging such immune reactions triggered by peptide-MHC complexes has recently shown substantial promise for peptide-based vaccines in the prevention of human diseases. Peptide-based vaccines have better stability and synthesizability when compared with large proteins and may trigger the desired immune responses with fewer side effects.

Despite recent successes, developing peptide-based immunotherapy still confronts a major challenge, that is, how to efficiently identify foreign binding peptides and binding motifs of given MHC proteins. To tackle this challenge, many computational tools predicting the binding affinities between peptides and MHC class I proteins have been developed. However, even with these tools, it is still difficult to directly find the qualified peptides that can be presented by specific MHC proteins for computing binding motifs. It becomes even more challenging because some MHC proteins have no or limited experimental data due to the high cost to obtain them. In practice, to find all the qualified peptides for binding motif identification with the existing computational tools, it may be needed to exhaustively screen all possible peptides. This screening is time-consuming and costly.

To address such challenge, the exemplary embodiments formulate the foreign peptide search as a standard search problem and propose a system composed of several search methods to generate qualified peptides and peptide binding motifs.

In view thereof, the exemplary embodiments present four search methods with peptide generation to generate these qualified peptides. These four search methods are Monte Carlo Tree Search (MCTS), Bayesian Optimization with a Variational Autoencoder (BO-VAE), Backpropagation with a Variational Autoencoder (BP-VAE), and sampling from a Position Weight Matrix (sPWM). If a pre-defined library of peptides derived from the genome of a virus such as SARS-COV-2 or from sequencing tumor samples of a patient is provided, the search methods based on MCTS, BO-VAE, and BP-VAE can be used for generating qualified peptides for immunotherapy with pre-defined peptides as starting peptides (seeds).

Given a virus genome or some tumor cells, the exemplary methods run sequencing followed by some off-the-shelf peptide processing pipelines to extract a library of peptides that can uniquely identify the virus or tumor cells.

The MCTS method for peptide generation is as follows, $c_{puct}$ is set to 0.5.

Regarding the MCTS method, each state is a sequence of amino acids. The root state is the empty sequence.

For each state, one amino acid can be selected, and the next state can be obtained by appending it to the sequence of this state.

The amino acid that has the maximum value is selected with the UCB1 formula:

$$a_k = \arg \max_a \frac{\sum_i {}^i r_i}{N(s, a)} + c_{puct} * \sqrt{\frac{2N(s)}{1 + N(s, a)}}$$

where $c_{puct}$ is the tradeoff between exploitation and exploration, $N(s,a)$ is the visit count of state-action pair, $N(s)$ is the visit count of state s, and $r_i$ is the maximum representation score of the i-th rollout through the state-action pair.

The new state will be added to the tree.

For each state s with sequence of length l≥8, the exemplary methods can use, e.g., MHCFlurry 2.0 to evaluate the presentation score of that sequence p(s).

The terminal state has the sequence of length l=15.

After reaching the terminal state, the exemplary methods backpropagate the presentation score $$r_i^{t-1} = \max\left(r_i^t, p\left(s_i^{t-1}\right)\right)$$

in which $$r_i^T = p\left(s_i^T\right).$$

In both BO-VAE and BP-VAE, the exemplary methods first train a Variational Autoencoder (VAE) to reconstruct all possible peptides in a database, by which a peptide sequence is converted into a continuous embedding vector. Then a Multi-Layer Perceptron (MLP) is trained to predict presentation scores of peptides from the peptide embedding inputs for each allele (the MLP predictor is allele-specific). After that, a Bayesian Optimization or Backpropagation is applied to maximize the presentation score over peptide embeddings.

The BO-VAE method works as follows:

---

Algorithm 1 Basic pseudo-code for Bayesian optimization

---

Place a Gaussian process prior on f
Observe f at $n_S$ points according to an initial space-filling experimental design. Set $n = n_S$.
while n ≤ N do
    Update the posterior probability distribution on f using all available data
    Let $x_n$ be a maximizer of the aquisition function over x, where the acquisition fuction is computed using the current posterior distribution. Observe $y_n = f(x_n)$.
    Increment n
end while
Return a solution either the point evaluated with the largest f(x), or the point with the largest posterior mean.

---

In BO-VAE, a VAE model is pre-trained to convert peptide sequences of variable lengths into continuous embeddings of a fixed size. The reconstruction accuracy of peptide sequences with this VAE model is above 95%. Given an allele, the Bayesian optimization algorithm with Radial Basis Function (RBF) kernel is then employed to optimize random latent embeddings with maximum t steps so that the peptide sequences decoded from the optimized latent embeddings are with the high presentation scores. At each step, BO-VAE evaluates the presentation scores of the generated peptides with, e.g., MHCflurry2.0 and stops the optimization and outputs the peptides if their presentation scores are greater than a threshold.

For BP-VAE, a student model with the variational autoencoder, same as that in the BO-VAE, is employed to learn the presentation scores from, e.g., MHCFlurry 2.0. After getting the trained student model, the BP-VAE can generate peptides by optimizing the latent embeddings of peptides through gradient ascent to maximize the predicted presentation scores from the student model. The decoded peptide sequences with t steps will be evaluated by, e.g., MHCFlurry 2.0.

In sPWM, for each MHC protein, sPWM generates peptides of length l by sampling from the amino acid distributions of all the l positions calculated from the positive presented peptides for that allele. To decide the length l of the generated peptides, the exemplary methods sample length 8 with the probability 15%, lengths 9-11 with probability 20%, length 12 with probability 10%, and lengths 13-15 with probability 5%, respectively. The probabilities are determined according to those most qualified peptides that have length from 8 to 11.

In conclusion, the exemplary embodiments introduce four search methods with peptide generation to generate qualified peptides that can be presented by given MHC alleles. If a pre-defined library of peptides derived from the genome of a virus such as SARS-Cov-2 or from sequencing tumor samples of a patient is provided, the search methods based on MCTS, BO-VAE, and BP-VAE can be used for generating qualified peptides for immunotherapy with pre-defined peptides as starting peptides (seeds). The system can be used for generating peptides for immunotherapy targeting a particular type of virus or tumor.

FIG. 1 is a block/flow diagram of an exemplary method for searching for peptide vaccine design for immunotherapy, in accordance with embodiments of the present invention.

At block 101, train a deep neural network or employ a pre-trained model to predict a peptide presentation given an MHC allele sequence and a peptide sequence.

At block 103, train a VAE to reconstruct peptides and generate new peptides, converting peptide sequences into continuous embedding vectors.

At block 105, targeting a MHC, run a Monte Carlo Tree Search (MCTS) to generate some (a first set of) peptide vaccine candidates, run a Bayesian Optimization and Back-propagation, and use the trained VAE decoder to generate some (a second set of) positive peptide vaccine candidates.

At block 107, targeting a MHC, use sPWM to generate some (a third set of) positive peptide vaccine candidates.

At block 109, use MHCFlurry 2.0 (or other deep neural network) to screen these merged positive peptide vaccine candidates (first, second, and third sets) to output a final set of positive peptides.

At block 111, output qualified peptides for immuno-therapy from the screened and merged sets of positive peptide vaccine candidates and calculate the binding motif for the target MHC based on the qualified peptides.

Figure 2:
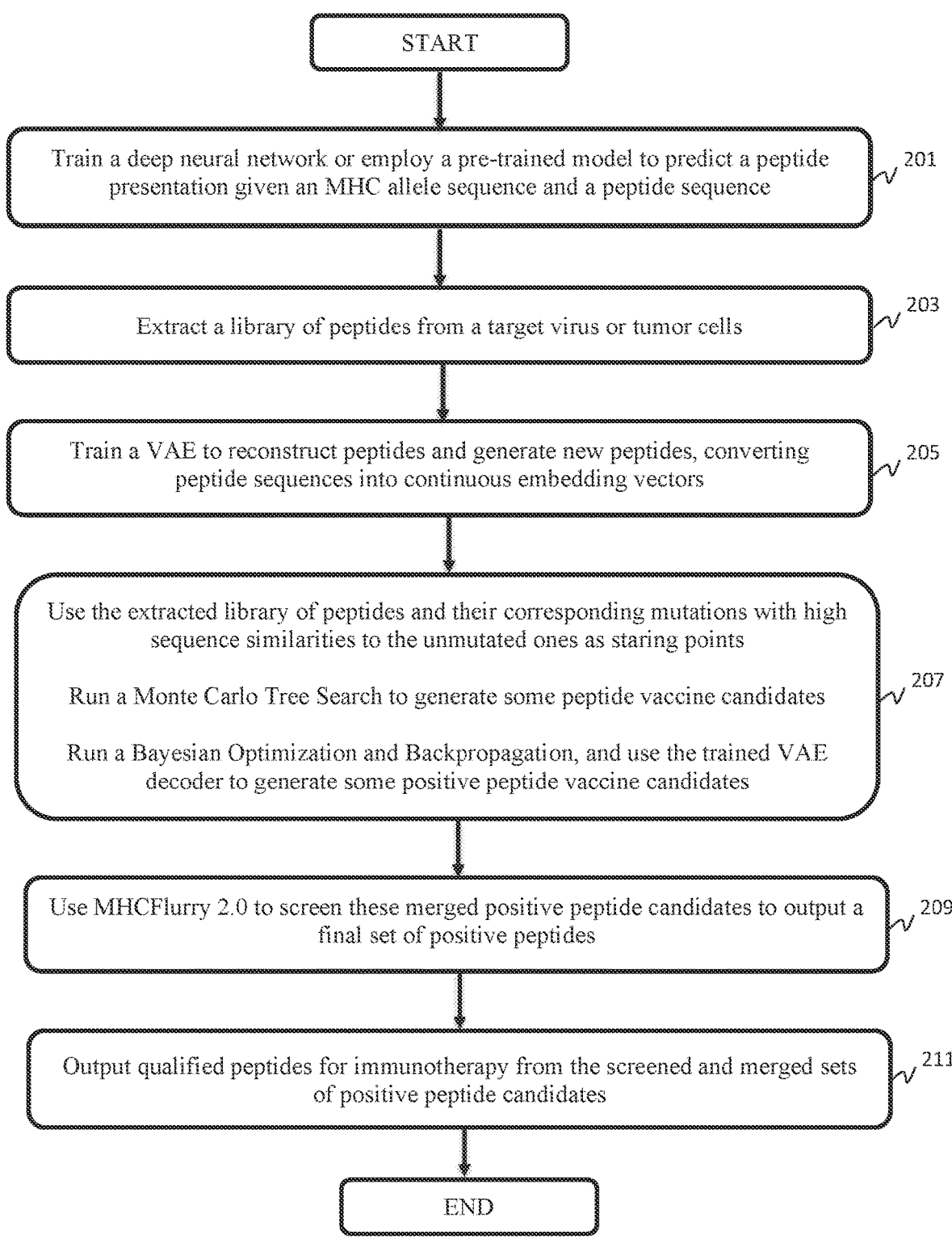
FIG. 2 is a block/flow diagram of an exemplary method for searching for peptide vaccine design targeting a library of peptides, in accordance with embodiments of the present invention.

FIG. 2 is a block/flow diagram of an exemplary method for searching for peptide vaccine design targeting a library of peptides, in accordance with embodiments of the present invention.

At block 201, train a deep neural network or employ a pre-trained model to predict a peptide presentation given an MHC allele sequence and a peptide sequence.

At block 203, extract a library of peptides from a target virus or tumor cells.

At block 205, train a VAE to reconstruct peptides and generate new peptides, converting peptide sequences into continuous embedding vectors.

At block 207, use the extracted library of peptides and their corresponding mutations with high sequence similarities to the unmutated ones as staring points, run a Monte Carlo Tree Search to generate some (a first set of) peptide vaccine candidates, run a Bayesian Optimization and Back-propagation, and use the trained VAE decoder to generate some (second set of) positive peptide vaccine candidates.

At block 209, use MHCFlurry 2.0 (or other deep neural network) to screen these merged positive peptide vaccine candidates to output a final set of positive peptides.

At block 211, output qualified peptides for immuno-therapy from the screened and merged sets of positive peptide vaccine candidates.

Figure 3:
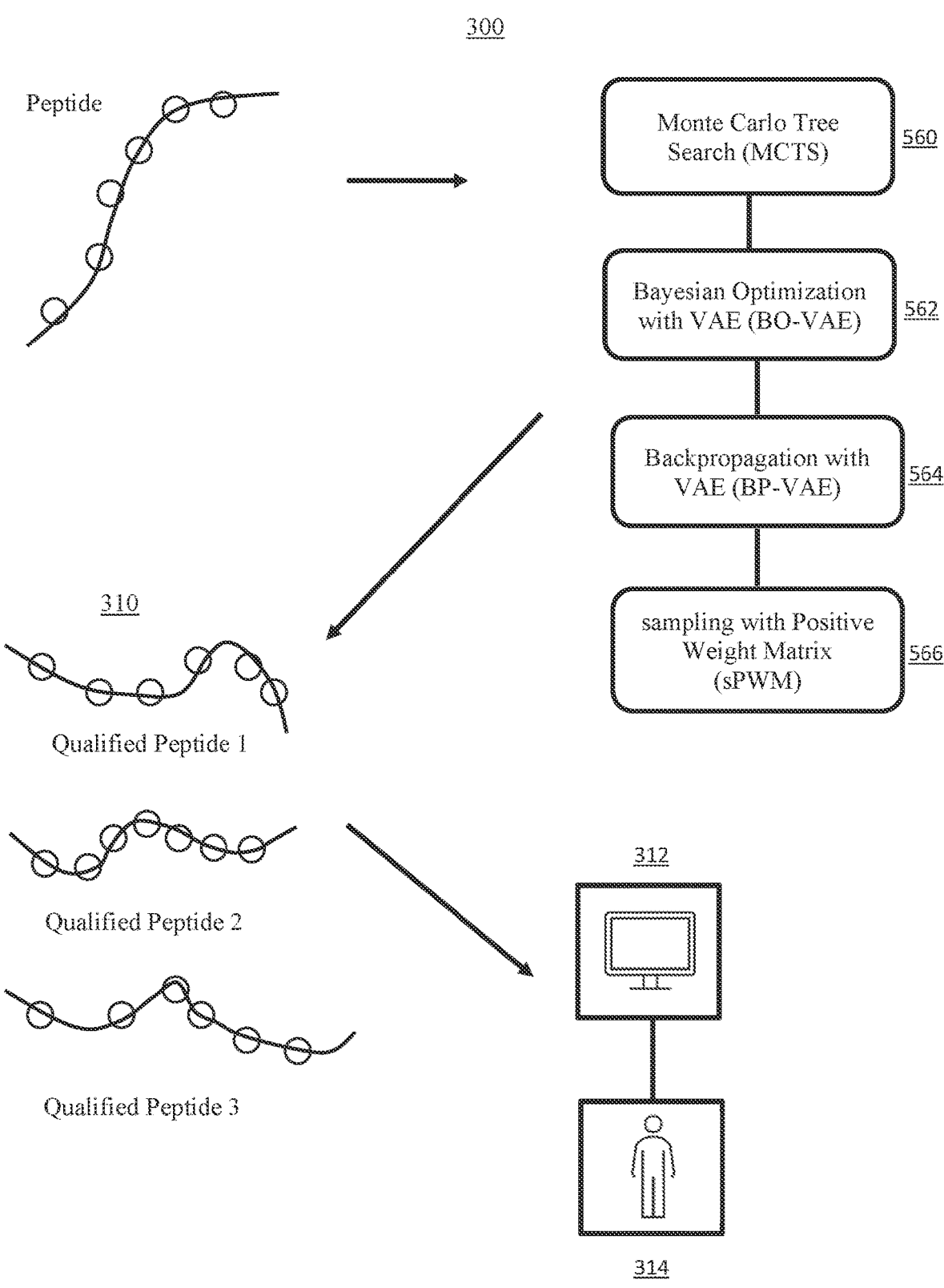
FIG. 3 is an exemplary practical application for searching for binding peptides for immunotherapy, in accordance with embodiments of the present invention.

FIG. 3 is an exemplary practical application 300 for searching for binding peptides for immunotherapy, in accordance with embodiments of the present invention.

In one practical example 300, a peptide is processed to generate new qualified peptides 310 to be displayed on a screen 312 and analyzed by a user 314. Our system employs the four search methods, that is MCTS 560. BO-VAE 562, BP-VAE 564, and sPWM 566.

Figure 4:
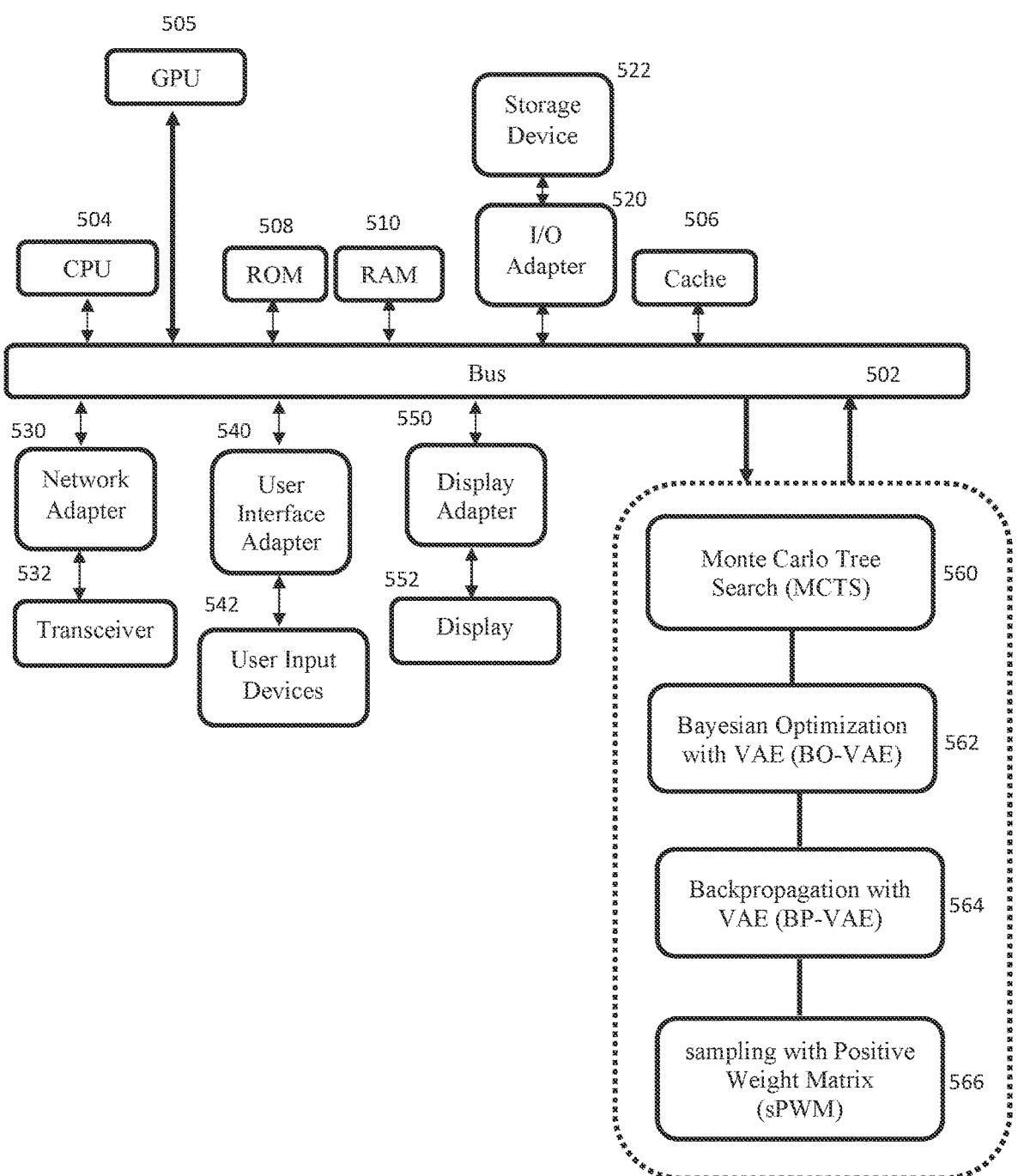
FIG. 4 is an exemplary processing system for searching for binding peptides for immunotherapy, in accordance with embodiments of the present invention.

FIG. 4 is an exemplary processing system for searching for binding peptides for immunotherapy, in accordance with embodiments of the present invention.

The processing system includes at least one processor (CPU) 504 operatively coupled to other components via a system bus 502. A Graphical Processing Unit (GPU) 505, a cache 506, a Read Only Memory (ROM) 508, a Random Access Memory (RAM) 510, an Input/Output (I/( ) adapter 520, a network adapter 530, a user interface adapter 540, and a display adapter 550, are operatively coupled to the system bus 502. Additionally, our system employs the four search methods, that is MCTS 560, BO-VAE 562, BP-VAE 564, and sPWM 566.

A storage device 522 is operatively coupled to system bus 502 by the I/O adapter 520. The storage device 522 can be any of a disk storage device (e.g., a magnetic or optical disk storage device), a solid-state magnetic device, and so forth.

A transceiver 532 is operatively coupled to system bus 502 by network adapter 530.

User input devices 542 are operatively coupled to system bus 502 by user interface adapter 540. The user input devices 542 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 542 can be the same type of user input device or different types of user input devices. The user input devices 542 are used to input and output information to and from the processing system.

A display device 552 is operatively coupled to system bus 502 by display adapter 550.

Of course, the processing system may also include other elements (not shown), as readily contemplated by one of skill in the art, as well as omit certain elements. For example, various other input devices and/or output devices can be included in the system, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system are readily contemplated by one of ordinary skill in the art given the teachings of the present invention provided herein.

In conclusion, the exemplary embodiments first train a deep neural network on the public IEDB dataset or employ a pre-trained model such as MHCFlurry 2.0 to predict a peptide presentation score (a combination of peptide-MHC binding affinity and antigen processing score) given an MHC allele sequence and a peptide sequence. Based on this pre-trained model for predicting peptide presentation scores from MHC allele and peptide sequences, the exemplary embodiments apply MCTS and sPWM to generate positive peptide vaccine candidates and use, e.g., MHCFlurry 2.0 to screen the positive peptides during the search process of MCTS and sPWM. A VAE model is pre-trained to convert peptide sequences of variable lengths into continuous latent embeddings of a fixed size. A student model, such as MLP, is trained to simulate MHCFlurry 2.0 predictions using the peptide embeddings as inputs. The exemplary embodiments apply Bayesian Optimization or Backpropagation on the peptide embeddings to maximize presentation scores. After a solution is found, the exemplary embodiments use the VAE to decode it into a generated peptide and use, e.g., MHCFlurry 2.0 to screen the generated peptides. Then these generated positive peptides are merged to output a final set of positive peptides. Finally, to target a pre-defined library of peptides derived from the genome of a virus such as SARS-COV-2 or from sequencing tumor samples of a patient, the search methods based on MCTS, BO-VAE, and BP-VAE can be used for generating qualified peptides for immunotherapy with pre-defined peptides as starting peptides (seeds).

As used herein, the terms "data," "content." "information" and similar terms can be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data can be received directly from the another computing device or can be received indirectly via one or more intermediary computing devices, such as, for example, one or more servers, relays, routers, network access points, base stations, and/or the like.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," "calculator," "device," or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non exhaustive list) of the computer readable storage medium would include the following: an electrical connection having one or more wires, a portable computer diskette, a hard disk, RAM, ROM, an Erasable Programmable Read-Only Memory (EPROM or Flash memory), an optical fiber, a portable CD-ROM, an optical data storage device, a magnetic data storage device, or any suitable combination of the foregoing. In the context of this document, a computer readable storage medium may be any tangible medium that can include, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk. C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or modules.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks or modules.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks or modules.

It is to be appreciated that the term "processor" as used herein is intended to include any processing device, such as, for example, one that includes a CPU and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. Such memory may be considered a computer readable storage medium.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for searching for binding peptides for immunotherapy, the method comprising:

training a deep neural network to predict a peptide presentation given Major Histocompatibility Complex (MHC) allele sequences and peptide sequences;

extracting a library of peptide sequences from a targeted tumor;

converting the peptide sequences with variable lengths into peptide embeddings having continuous embedding vectors of a fixed size;

training a Variational Autoencoder (VAE) to reconstruct peptides from peptide embeddings;

generating a first set of positive peptide vaccine candidates from the peptide embeddings based on a Monte Carlo Tree Search (MCTS);

generating a second set of positive peptide vaccine candidates from the peptide embeddings based on a Bayesian Optimization search with the trained VAE (BO-VAE) and a backpropagation search with the trained VAE (BP-VAE);

generating a third set of positive peptide vaccine candidates from the peptide embeddings with a sampling from a Position Weight Matrix (sPWM);

screening and merging the first, second, and third sets of positive peptide vaccine candidates into qualified peptides using the deep neural network; and generating the qualified peptides for immunotherapy that targets the targeted tumor by leveraging immune reactions triggered by peptide-MHC complexes from the screened and merged first, second, and third sets of positive peptide vaccine candidates.

2. The method of claim 1, further comprising training a Multi-Layer Perceptron (MLP) to predict presentation scores of the peptides from the peptide embeddings.

3. The method of claim 2, wherein the BO-VAE and the BP-VAE are employed to maximize the presentation scores of the peptides from the peptide embeddings.

4. The method of claim 1, wherein generating a second set of positive peptide vaccine candidates further comprises learning presentation scores from the deep neural network with the BP-VAE and generate a portion of the second set of positive peptide vaccine candidates by optimizing the peptide embeddings with a gradient ascent.

5. The method of claim 1, wherein generating a third set of positive peptide vaccine candidates further comprises the sPWM generates the second set of positive peptide vaccine candidates having a length l by sampling from amino acid distributions of all l positions calculated from the peptide embeddings.

6. The method of claim 1, wherein the peptides are extracted from a library of peptides of a target virus.

7. The method of claim 6, wherein the extracted library of peptides and corresponding mutations with sequence similarities to unmutated peptides are employed as starting points for the MCTS, the BO-VAE, the BP-VAE, and the sPWM.

8. A non-transitory computer-readable storage medium comprising a computer-readable program for binding peptides for immunotherapy, wherein the computer-readable program when executed on a computer causes the computer to perform the steps of:

training a deep neural network to predict a peptide presentation given Major Histocompatibility Complex (MHC) allele sequences and peptide sequences;

extracting a library of peptide sequences from a targeted tumor;

converting the peptide sequences with variable lengths into peptide embeddings having continuous embedding vectors of a fixed size;

training a Variational Autoencoder (VAE) to reconstruct peptides from peptide embeddings;

generating a first set of positive peptide vaccine candidates from the peptide embeddings based on a Monte Carlo Tree Search (MCTS);

generating a second set of positive peptide vaccine candidates from the peptide embeddings based on a Bayesian Optimization search with the trained VAE (BO-VAE) and a backpropagation search with the trained VAE (BP-VAE);

generating a third set of positive peptide vaccine candidates from the peptide embeddings with a sampling from a Position Weight Matrix (sPWM);

screening and merging the first, second, and third sets of positive peptide vaccine candidates into qualified peptides using the deep neural network; and generating the qualified peptides for immunotherapy that targets the targeted tumor by leveraging immune reactions triggered by peptide-MHC complexes from the screened and merged first, second, and third sets of positive peptide vaccine candidates.

9. The non-transitory computer-readable storage medium of claim 8, further comprising training a Multi-Layer Perceptron (MLP) to predict presentation scores of the peptides from the peptide embeddings.

10. The non-transitory computer-readable storage medium of claim 9, wherein the BO-VAE and the BP-VAE are employed to maximize the presentation scores of the peptides from the peptide embeddings.

11. The non-transitory computer-readable storage medium of claim 8, wherein generating a second set of positive peptide vaccine candidates further comprises learning presentation scores from the deep neural network with the BP-VAE and generate a portion of the second set of positive peptide vaccine candidates by optimizing the peptide embeddings with a gradient ascent.

12. The non-transitory computer-readable storage medium of claim 8, wherein generating a third set of positive peptide vaccine candidates further comprises the sPWM generates the second set of positive peptide vaccine candidates having a length 1 by sampling from amino acid distributions of all 1 positions calculated from the peptide embeddings.

13. The non-transitory computer-readable storage medium of claim 8, wherein the peptides are extracted from a library of peptides of a target virus.

14. The non-transitory computer-readable storage medium of claim 13, wherein the extracted library of peptides and corresponding mutations with sequence similarities to unmutated peptides are employed as starting points for the MCTS, the BO-VAE, the BP-VAE, and the sPWM.

15. A system for binding peptides for immunotherapy, the system comprising:

a memory; and one or more processors in communication with the memory configured to:

train a deep neural network to predict a peptide presentation given Major Histocompatibility Complex (MHC) allele sequences and peptide sequences;

extract a library of peptide sequences from a targeted tumor;

convert the peptide sequences with variable lengths into peptide embeddings having continuous embedding vectors of a fixed size:

train a Variational Autoencoder (VAE) to reconstruct peptides from peptide embeddings;

generate a first set of positive peptide vaccine candidates from the peptide embeddings based on a Monte Carlo Tree Search (MCTS);

generate a second set of positive peptide vaccine candidates from the peptide embeddings based on a Bayesian Optimization search with the trained VAE (BO-VAE) and a backpropagation search with the trained VAE (BP-VAE);

generate a third set of positive peptide vaccine candidates from the peptide embeddings with a sampling from a Position Weight Matrix (sPWM);

screen and merge the first, second, and third sets of positive peptide vaccine candidates into qualified peptides using the deep neural network; and generate the qualified peptides for immunotherapy that targets the targeted tumor by leveraging immune reactions triggered by peptide-MHC complexes from the screened and merged first, second, and third sets of positive peptide vaccine candidates.

16. The system of claim 15, further comprising training a Multi-Layer Perceptron (MLP) to predict presentation scores of the peptides from the peptide embeddings.

17. The system of claim 16, wherein the BO-VAE and the BP-VAE are employed to maximize the presentation scores of the peptides from the peptide embeddings.

18. The system of claim 15, wherein generating a second set of positive peptide vaccine candidates further comprises learning presentation scores from the deep neural network with the BP-VAE and generate a portion of the second set of positive peptide vaccine candidates by optimizing the peptide embeddings with a gradient ascent.

19. The system of claim 15, wherein generating a third set of positive peptide vaccine candidates further comprises the sPWM generates the second set of positive peptide vaccine candidates having a length 1 by sampling from amino acid distributions of all 1 positions calculated from the peptide embeddings.

20. The system of claim 15, wherein the peptides are extracted from a library of peptides of a target virus.

\*   \*   \*   \*   \*